United States Patent [19]

Melgaard et al.

[11] Patent Number: 5,516,489

[45] Date of Patent: May 14, 1996

[54] APPARATUS FOR TESTING PEROXIDE CONCENTRATIONS IN STERILANTS

[75] Inventors: Hans L. Melgaard, North Oaks; Louis A. Larson, Golden Valley, both of Minn.

[73] Assignee: Despatch Industries, Inc., Minneapolis, Minn.

[21] Appl. No.: 109,274

[22] Filed: Aug. 19, 1993

[51] Int. Cl.[6] .................................................. G01N 7/18
[52] U.S. Cl. .................... 422/82.13; 422/68.1; 422/78; 422/80; 436/135; 436/148; 436/181
[58] Field of Search .................. 422/27, 68.1, 78, 422/80, 82.13; 436/38, 135, 148, 181

[56] References Cited

U.S. PATENT DOCUMENTS

| | | | |
|---|---|---|---|
| 2,832,673 | 4/1958 | Larson et al. | 436/38 |
| 3,917,461 | 11/1975 | Kühl et al. | 422/190 |
| 3,973,912 | 8/1976 | Trafton et al. | 436/148 X |
| 4,601,884 | 7/1986 | Coeckelberghs et al. | 422/113 |
| 4,642,165 | 2/1987 | Bier | 422/27 X |
| 4,792,435 | 12/1988 | Nakajima | 422/110 |
| 4,992,247 | 2/1991 | Foti | 422/31 X |
| 5,081,045 | 1/1992 | McGill | 436/148 X |

FOREIGN PATENT DOCUMENTS

| | | |
|---|---|---|
| 0052834 | 6/1982 | European Pat. Off. . |
| 3636716 | 5/1988 | Germany . |
| 55-104757 | 8/1980 | Japan ............................. 436/148 |

OTHER PUBLICATIONS

J. C. Farmer et al. *J. Geophys. Research*, 1982, 87, 8931–8942.
P. Jacob et al. *Fregenius Z. Anal. Chem.* 1986, 325, 359–364.
E. Quitman et al. *Helv. Chim. Acta.* 1939, 116, 81–91.
R. J. Wiley et al. *Chem. Abstr.* 1963, 59, 4585c.
J. Schubert et al. *J. Am. Chem. Soc.* 1968, 90, 4476–4478.
V. S. Sharma et al. *J. Am. Chem. Soc.* 1970, 92, 822–826.
T. Moriyoshi *Bull. Chem. Soc. Japan* 1971, 44, 2582–2587.
A. C. Melnyk et al. J. Am. Chem. Soc. 1979, 101, 3232–3240.

*Primary Examiner*—James C. Housel
*Assistant Examiner*—Arlen Soderquist
*Attorney, Agent, or Firm*—Fredrikson & Byron

[57] ABSTRACT

An apparatus for testing peroxide concentration in a gaseous sterilant. A preferred embodiment of the apparatus includes a condenser for condensing the gaseous sterilant into a liquid condensate; an aliquot collector of predetermined volume to receive the condensate; a reaction chamber containing a catalyst for dissociating the peroxide; and a pressure monitor for detecting pressure changes in the reaction chamber as a function of time. The pressure monitor of this apparatus is capable of detecting a threshold pressure and an upper pressure and it includes a timer to measure time change between detection of the threshold pressure and the upper pressure.

13 Claims, 2 Drawing Sheets

5,516,489

APPARATUS FOR TESTING PEROXIDE CONCENTRATIONS IN STERILANTS

FIELD OF THE INVENTION

The present invention generally relates to means and methods of sterilizing or decontaminating equipment and the like and has particular utility for use in connection with the use of a gaseous sterilizing agent containing peroxide.

BACKGROUND OF THE INVENTION

A variety of different systems for sterilizing or decontaminating materials. For example, some industries must maintain equipment used in the production or packaging facilities at relatively low levels of decontamination to avoid contamination of the products by microbial agents and the like. One prime example of such an industry is the pharmaceutical industry, which must routinely fill containers in a decontaminated environment with decontaminated equipment to avoid introducing any microbial agents into the pharmaceutical products being packaged.

There are a number of accepted sterilizing agents used in these operations. One sterilant which has been found to work well is a mixture of hydrogen peroxide and some other element, such as saturated steam. Such hydrogen peroxide sterilants are usually applied in a gaseous form (e.g mixed with saturated steam) in an enclosed environment.

It may be desirable to test the nature of the sterilant at some point or points during or after the sterilization procedure to ensure that the sterilant is effective. In the case of a peroxide-containing sterilant, it may be desirable to measure the concentration of the peroxide in the mixture used as the sterilizing agent. However, it has proven difficult to reliably and cheaply check hydrogen peroxide concentration of a sterilant in a commercial setting. Although mass spectroscopy can be used to detect the presence and concentration of hydrogen peroxide, it is generally too expensive to dedicate a mass spectrometer to a specific decontamination station. To date, there does not appear to be a satisfactory method of quickly, reliably and cheaply checking hydrogen peroxide concentration in a sterilant in a commercial production setting.

SUMMARY OF THE INVENTION

The present invention provides a means and method of testing peroxide concentration in a gaseous sterilant. One embodiment of the invention provides an apparatus for measuring peroxide concentration in a gaseous sterilant. This apparatus includes a condenser for condensing the gaseous sterilant into a liquid condensate; an aliquot collector of predetermined volume receiving condensate from the condenser; a catalyst for dissociating the peroxide in the aliquot; a pressure monitor for detecting pressure changes resulting from the peroxide dissociation as a function of time, which pressure change is correlated to the concentration of peroxide in the sterilant. The apparatus may include a collection and testing tube disposed beneath the condenser, with a series of valves defining the aliquot collector and a reaction vessel along the length of the tube, with the catalyst being disposed in the reaction vessel.

In another embodiment, the invention provides a method for measuring peroxide concentration in a gaseous sterilant. In accordance with this embodiment, the gaseous sterilant is condensed into a liquid condensate; a predetermined volume of the condensate is placed into a reaction chamber having a predetermined volume; a catalyst in the reaction chamber is allowed to dissociate the peroxide; the pressure change resulting from said dissociation is measured as a function of time; and the rate of pressure change in the reaction chamber is correlated with concentration of peroxide in the sterilant. In a further embodiment, a quantity of gaseous sterilant in a sterilizing enclosure is removed from the enclosure and passed over a condenser. The rate of pressure change may be measured by detecting a first predetermined pressure and a second predetermined pressure, the second pressure being greater than the first pressure, and measuring the time between detecting the first pressure and detecting the second pressure.

DETAILED DESCRIPTION OF PREFERRED EMBODIMENTS

Figure 1:
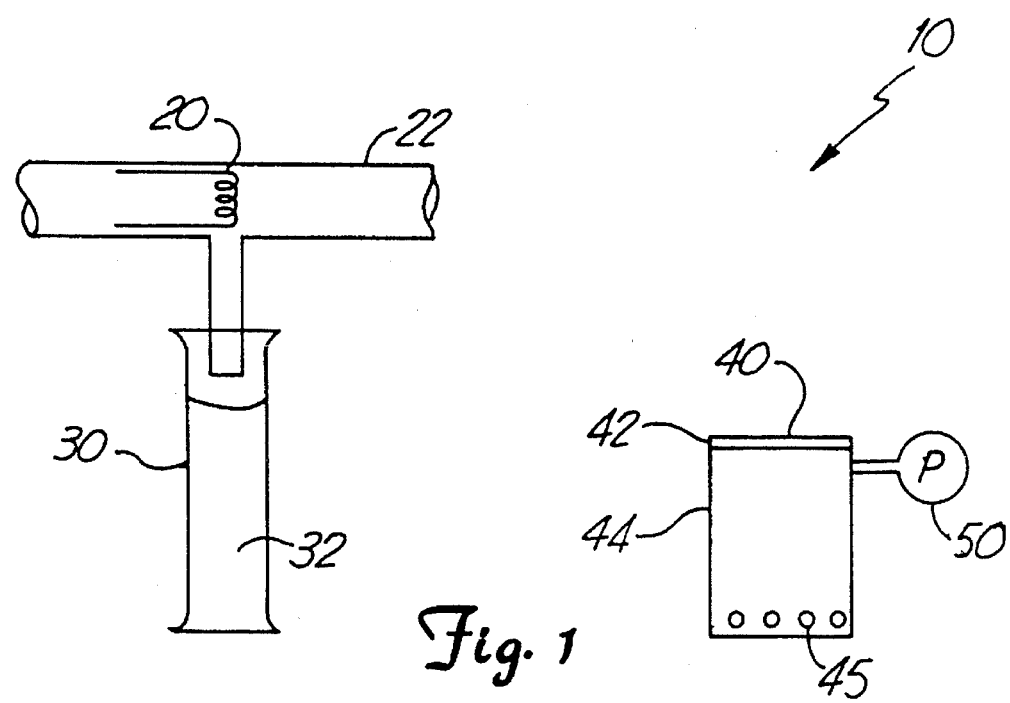
FIG. 1 is a schematic illustration of an apparatus in accordance with the invention.

FIG. 1 schematically depicts an apparatus for measuring peroxide concentration in a sterilant in accordance with the invention. This diagram functionally shows the elements of the invention and an analogous system may be used in conducting either manual or automated measurements. The system 10 of FIG. 1 generally includes a condenser 20, an aliquot collector 30, a reaction chamber 40, a catalyst 45 and a pressure monitor 50.

The condenser 20 is schematically shown in FIG. 1 as a coil, but any suitable means of condensing a gaseous sterilant to be tested with the system 10 may be used. For instance, the condenser may comprise a convention coil-type condenser in which the gaseous sterilant is passed through a coiled tube in a cooling medium to reduce the temperature of the sterilant to below its boiling point. Alternatively, the condenser could comprise a cold plate, maintained at a temperature below the boiling point of the sterilant, positioned in the stream of a supply sterilant. As the sterilant passes over the cold plate it will tend to condense on the surface of the plate and the condensed sterilant may be directed along the surface of the plate into a tube or the like for collection. Other mechanisms capable of condensing the sterilant will be obvious to those of ordinary skill in the art.

The condenser may be placed into contact with the sterilant in any suitable fashion. In FIG. 1, for example, a supply conduit 22 may lead from the condenser to a sterilizing enclosure (not shown) or to a sterilant supply (not shown). A sample of the sterilant may be obtained by, e.g. withdrawing some of the sterilant from the sterilizing enclosure through the supply conduit 22. In one preferred embodiment, the sterilant is removed from the sterilizing enclosure during the sterilization or decontamination process. The supply conduit may direct any uncondensed sterilant back into the enclosure, but if so care should be taken to ensure that the condenser and the like are suitably decontaminated to ensure that no unwanted contamination is introduced into the enclosure.

Figure 2:
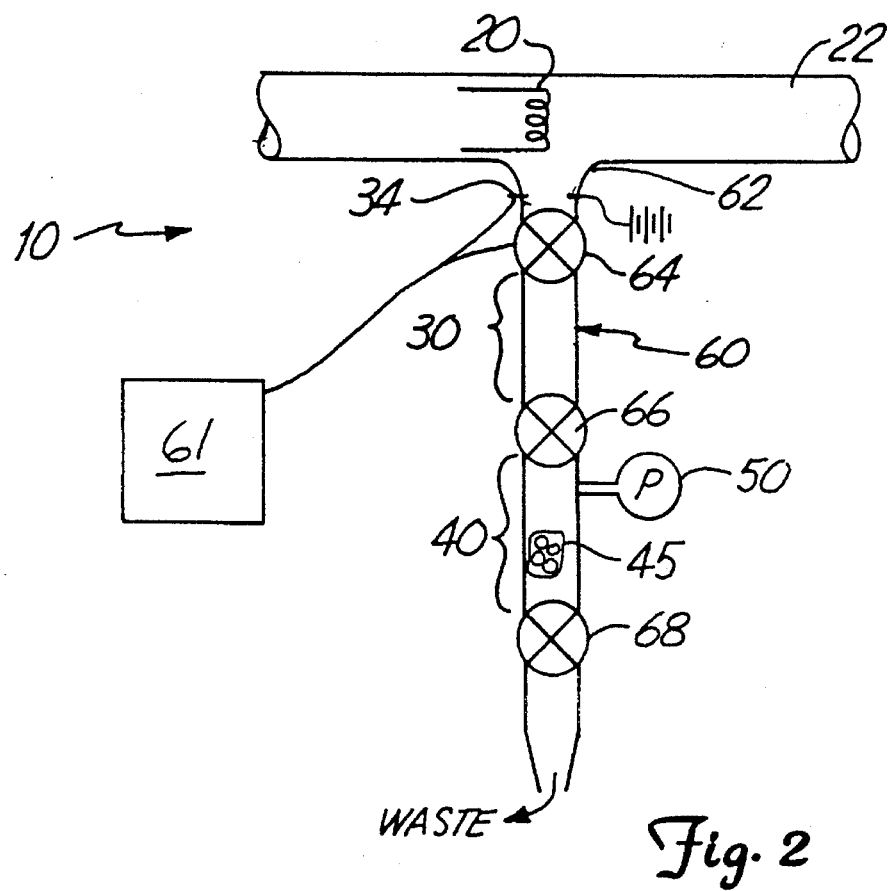
FIG. 2 is a schematic illustration of an apparatus in accordance with the invention useful in making automated measurements of peroxide concentration.

Condensed sterilant can be directed to an aliquot collector 30 having a predetermined volume for collecting an aliquot 32 of condensate having a suitable predetermined volume. In the embodiment illustrated in FIG. 1, the aliquot collector 30 is a separate container which may receive condensed sterilant from the condenser by means of a tube or the like, but is physically separable from the condenser. In the embodiment of FIG. 2, discussed more fully below, the aliquot collector 30 is physically connected to an enclosure about the condensing mechanism. The aliquot collector may be of any suitable design, such as a graduated container having a marking defining the predetermined volume of the desired aliquot of condensate.

The aliquot 32, which has a substantially fixed, predetermined volume, may then be transferred into a reaction chamber 40, which has a second predetermined volume. The volume of the reaction chamber should be sufficient to receive the entire aliquot 32 from the aliquot collector, desirably leaving a headspace of known volume above the aliquot in the reaction chamber. In the embodiment shown in FIG. 1, the reaction chamber comprises a base 44 which optimally defines the interior of the chamber 40 and a removable cap 42 which may be removed to permit the aliquot to be added to the chamber. The cap should fit the base with a substantially air-tight seal and be configured so that the interior volume of the sealed container is consistent from one run of the testing procedure to the next. Having a threaded connection with an o-ring seal, for example, should suffice.

A catalyst 45 is optimally placed in the reaction chamber to promote the dissociation of peroxide in the aliquot of condensed sterilant. The dissociation of the peroxide will generally yield oxygen and a reaction byproduct which may depend of the nature of the peroxide. For instance, in the case of hydrogen peroxide, the dissociation reaction may be expressed generally as Formula 1:

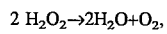

$$2 H_2O_2 \rightarrow 2H_2O + O_2,$$

with the oxygen being in gaseous form. This oxygen gas will tend to increase the pressure in the enclosed reaction chamber, yielding a detectable pressure change generally proportional to the volume of oxygen generated.

The catalyst should be selected to yield an appropriately accelerated rate of reaction to permit the measurement of the resulting pressure change in a suitable period of time. For instance, in the case of sterilants including hydrogen peroxide surface acting catalysts will generally suffice. Examples of such surface acting catalysts which should work well in connection with the invention include magnesium oxide, platinum and even stainless steel or the like. These catalysts may be finely divided solid particles of the catalytic material. However, in the case of platinum, for example, solid catalyst may be too expensive. In such cases, the catalyst may be provided as a coating on a crenelated support, such as platinum electroplate on a shaped piece of a plastic material. This will help maximize the surface area of the catalyst and thereby minimize the weight of the catalyst needed.

FIG. 1 illustrates the aliquot collector 30 and the reaction chamber 40 as separate elements of the system. It is to be understood, though, that the collector 30 and the reaction chamber 40 can be combined into one single container. In such an embodiment, the catalyst 45 may be placed in the aliquot collector 30 and the collector may be provided with a cap similar to cap 42 for sealing the top of the collector once an aliquot of the desired volume has been collected.

The pressure change in the sealed aliquot (which serves as the reaction chamber when it is sealed) can the be measured as outlined below.

The reaction chamber 40 is provided with a pressure monitor 50 for detecting pressure changes in the reaction chamber as a function of time. As noted above, dissociation of the peroxide yields oxygen, which increases the temperature. If the chamber is maintained at a substantially constant temperature, the rate of change in pressure in the chamber will be determined by the rate of dissociation of the peroxide. The rate of dissociation is related to the concentration of peroxide in the sterilant—a higher concentration of peroxide will drive the reaction set forth in Formula 1 toward the right at a greater rate. Accordingly, the rate of pressure change in the reaction chamber 40 at a specific temperature can be correlated to the concentration of peroxide in the sterilant by comparing the rate of pressure change determined by the pressure monitor 50 with rates of pressure change for known peroxide concentrations.

The pressure monitor may be operated in any suitable fashion. In the manual testing system schematically depicted in FIG. 1, for example, an operator may manually read the pressure from a display on the pressure monitor and note the rate at which pressure changes over time. The rate could be manually determined by simply noting the time required for a predetermined pressure change or the pressure change in a predetermined period of time.

In a preferred method, though, the pressure monitor is used to detect a predetermined threshold pressure and an predetermined upper measuring pressure. The threshold pressure is desirably greater than ambient pressure (i.e. >0 psig) so that the initial pressure in the reaction chamber will be below this threshold pressure and will exceed this threshold pressure only when the pressure in the reaction chamber increases, e.g. due to dissociation of the peroxide. A threshold pressure of about 0.2" WC (two tenths of one inch water column) has been found to work well for this purpose. The upper pressure should also be within the safe internal pressure of the reaction chamber. An upper pressure of about 1" WC has been determined to be suitable.

A timer may be started when the pressure in the reaction chamber reaches the threshold pressure and stopped when the pressure reaches the upper pressure. The time lapse as measured by this timer for this predetermined pressure change can them be compared to a set of known times for the same pressure change for known peroxide concentrations and the concentration of peroxide in the sterilant being tested can be interpolated from this set of known times.

FIG. 2 schematically illustrates an embodiment of the invention which may be useful in conducting automated testing of peroxide concentrations in sterilants. In FIG. 2, elements having functions analogous to the elements of FIG. 1 bear like reference numbers. In this embodiment, the condenser is positioned generally vertically above a collection and testing tube, generally designated 60. The tube may optimally have a flared-out neck portion 62 to direct condensate into the tube as it drips downwardly from the condenser 20.

The tube is provided with a series of three valves 64, 66 and 68 spaced along the length of the tube. Each of these valves has an open position wherein fluid is permitted to flow through the valve and a closed position for blocking flow through the section of the tube controlled by the valve. This permits the flow of condensate through the tube 60 to be controlled in stages by selectively controlling the position of the valves.

The first valve 64 is disposed along the tube generally toward the condenser 20 and the second valve is disposed along the tube at a location spaced below the first valve. The space between the first and second valves defines a predetermined volume along the section of the tube when these two valves are closed. This first segment of the tube serves as the aliquot collector 30 of the invention.

When condensate dripping downwardly from the condenser 20 is being accumulated in the aliquot collector 30, the first valve 64 remains in its open position and the second valve is in its closed position. When the level of the condensate in the aliquot collector reaches of exceeds the level of the first valve 64, the first valve may be closed to enclose an aliquot having a predetermined volume in the aliquot collector 30. The first valve may be manually controlled, as where an operator visually monitors the level of condensate in the tube and closes the first valve when the condensate level meets or exceeds the level of the first valve along the tube.

In a preferred embodiment, though, the first valve is automatically closed when the fluid meets or exceeds the level of the first valve. As schematically shown in FIG. 2, a level sensor 34 may be positioned along the length of the tube slightly above the height of the first valve. When this level sensor detects fluid above the first valve it may actuate a valve control motor 61 which turns the valve 62 to its closed position.

In the embodiment illustrated, the level sensor could, for example, comprise a pair of electrodes generally diametrically opposed from one another and extending into the interior of the tube, with a gap between the electrodes. When the level of the sterilant meets the height of the level sensor, the conductive condensate will fill the gaps between electrodes and thereby complete an electrical circuit to generate a signal that the aliquot collector 30 is full. When the first valve is closed, condensate will fill the entire length of the tube 60 between the first valve 64 and the second valve 66.

Once the first valve is closed after the aliquot collector 30 is full, the second valve 66 may be opened. This will allow the aliquot of condensate to flow through the second valve. At this stage, the third valve 68 is in its closed position, so the condensate will fill the tube between the second and third valves. The second valve may then be closed to substantially seal the length of the tube 60 between these two valves, effectively defining the reaction chamber 40 of the invention. As noted above, the reaction chamber is desirably large enough to receive the desired aliquot volume. If the tube 60 has a substantially constant internal diameter, the distance between the second and third valves 66,68 is desirably at least as great as the distance between the first and second valves 64,66.

The catalyst may be added to this reaction chamber 40 in any suitable manner. If the catalyst is in small enough particles to pass through the third valve, or is in solution, the catalyst will need to be added to the reaction chamber for each aliquot of sterilant to be tested. It is preferred, though, that the catalyst remain in the reaction chamber 40 when the chamber is flushed after testing (as described below). This may be accomplished by, for example, making the catalyst large enough to make sure that it cannot pass through the third valve. Alternatively, it may be held in a porous enclosure (schematically illustrated at 46 in FIG. 2) that permits the sterilant to enter the enclosure during testing but will retain the by in the enclosure when the chamber 40 is flushed.

As noted above, the rate of pressure change in the reaction chamber is optimally measured at a substantially constant pressure to ensure that temperature variations do not interfere with the accurate measurement of the rate of pressure change. Furthermore, the concentration of peroxide may be determined by comparing the measured rate of pressure change with a standardized calibration curve and this calibration curve is desirably an isothermal curve, with each calibration measurement taken at approximately the same temperature.

As the rate of the dissociation reaction proceeds (and hence the rate at which pressure increases) is temperature dependent, the temperature at which the pressure measurements are made is optimally approximately the same as the temperature at which the calibration measurements were made. In order to ensure such consistent measurements, it may be desirable to maintain the reaction chamber or, perhaps, the entire length of the tube 60 in a temperature controlled enclosure held at a substantially constant predetermined temperature.

The pressure may then be monitored as outlined generally above and the concentration of peroxide in the aliquot of sterilant may be determined. Once the concentration is determined, the third valve can be opened to permit the sterilant to flow out of the tube and into a drain or a waste collector for collecting the waste for suitable disposal.

Figure 3:
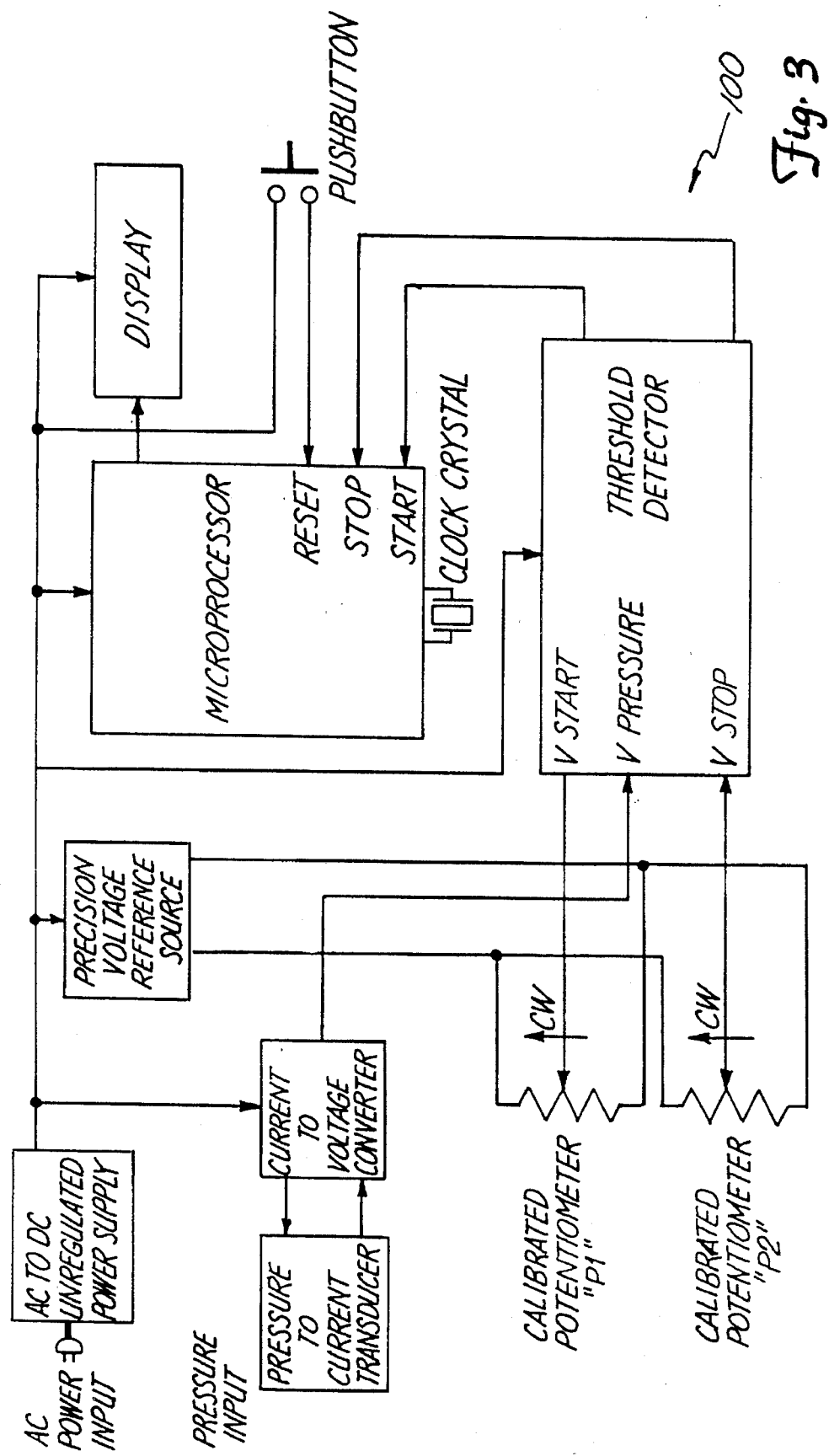
FIG. 3 is an electrical schematic diagram of a circuit useful in connection with the pressure monitor of the invention.

The schematic diagram of FIG. 3 illustrates an electrical system 100 which can be used in detecting pressure changes in the reaction chamber 40 and correlating these changes with concentration of peroxide in the sterilant. This circuit may form a portion of a pressure monitor 50 useful in connection with the present invention and has particular utility in the automatable system 10 of FIG. 2.

As illustrated at the left side of FIG. 3, the system 100 includes a transducer for converting pressure measurements to current measurements; such transducers are commercially available. This transducer is operatively connected to the reaction chamber 40 to permit the transducer to detect the pressure in the chamber. The current generated by the transducer is converted into a voltage signal which is proportional to the pressure in the chamber 40.

The voltage reference source generates two reference voltages, V1 and V2, with V1 being set to correspond to a preselected low pressure and V2 being set to correspond to a preselected high pressure. For instance, V1 may be set to correspond to the voltage level generated when the pressure in the reaction chamber 40 is about 0" WC and V2 may be set to correspond to the voltage level generated when the pressure in the reaction chamber 40 is about 1" W C.

These voltage levels V1 and V2 connect across two calibratable potentiometers P1 and P2. These potentiometers are set to produce "Vstart" and "Vstop" voltages corresponding to pressures between the pressures corresponding to V1 and V2 (e.g. between about 0" WC and about 1" WC). The Vstart voltage desirably corresponds to the predetermined threshold pressure outlined above, while the Vstop pressure desirably corresponds to the predetermined upper measuring pressure noted above. For example, the Vstart voltage may correspond to the pressure resulting from a 0.2" WC internal pressure in the reaction chamber and the Vstop voltage may correspond to the pressure resulting from a 1.0" WC internal pressure in the reaction chamber.

The threshold detector in FIG. 3 is operatively connected to a microprocessor, which includes means for measuring time changes, such as a crystal-controlled clock oscillator. Initially, the pressure in the reaction chamber 40 should be below the threshold pressure. The threshold detector sends a START signal to the microprocessor upon detecting the Vstart voltage from the current to voltage converter, i.e. Vpressure, to begin measuring time. When the threshold detector detects a voltage equal to the Vstop voltage, it will send a STOP signal to the microprocessor telling it to stop the time measurement.

In one preferred embodiment, this time lapse measured by the microprocessor may be displayed for an operator to read on a visual display, such as the "Display" noted in FIG. 3. The operator may then use measured time lapse and a table or plot of known time lapses for known peroxide concentrations to determine the concentration of peroxide in the sterilant, as noted above. In an alternative embodiment, the microprocessor includes a series of such known times for known concentrations and calculates a peroxide concentration measurement for the sterilant being tested. This calculated value could then be conveyed to an operator, such as via the display in FIG. 3, and may also be stored on a computer disk or the like for later retrieval.

In another embodiment, the present invention provides a method of detecting peroxide in a gaseous sterilant and measuring the concentration of that peroxide. If so desired, the method of the invention may be carried out utilizing a system 10 substantially as set forth above in connection with FIGS. 1 and 2. In accordance with the method of the invention, a gaseous sterilant is provided, such as in a sterilization or decontamination enclosure or from a supply for such an enclosure. This gaseous sterilant is condensed into a liquid condensate, such as by extracting a quantity of the sterilant from an enclosure and passing it over a suitable condenser, such as the condenser 20 outlined above.

A predetermined volume of this condensate is then placed into a suitable enclosed reaction chamber having a predetermined volume. In a preferred embodiment, an aliquot of the condensate is collected in an aliquot collector of predetermined volume and transferred into a separate reaction chamber. However, as noted above, the aliquot collector and the reaction chamber may be one and the same physical structure and there obviously would be no need to transfer the condensate in such an embodiment.

A catalyst in the reaction chamber is allowed to contact the sterilant to accelerate dissociation of the peroxide. The change in pressure in the reaction chamber resulting from the dissociation of the peroxide can be measured as a function of time and correlated with a concentration of peroxide in the sterilant, e.g. by comparing the rate of pressure change in the chamber against a table or plot of known rates for known peroxide concentrations. Optimally, the temperature within the reaction chamber is maintained at a fairly constant temperature to ensure reliable pressure data. As noted above, this may be achieved, e.g. by maintaining the reaction chamber in a controlled temperature environment.

The pressure monitoring and correlation with peroxide concentration may be carried out in any suitable manner. In a preferred embodiment, though, a timer is initiated when the pressure in the reaction chamber exceeds a predetermined threshold pressure (e.g. 0.2" WC) and the timer is stopped when a predetermined upper pressure (e.g. 1.0" WC) is reached. The time between the threshold pressure and reaching the upper pressure in the container can then be correlated to a measurement of peroxide concentration in the sterilant. As noted above, this correlation may be carried out by comparing the measured time lapse with a series of known time values for known peroxide concentrations.

While a preferred embodiment of the present invention has been described, it should be understood that various changes, adaptations and modifications may be made therein without departing from the spirit of the invention and the scope of the appended claims.

What is claimed is:

1. An apparatus for measuring peroxide concentration in a gaseous sterilant, comprising:
   a. a condenser for condensing the gaseous sterilant into a liquid condensate;
   b. a collection and testing tube disposed beneath the condenser;
   c. a first valve disposed along the tube toward the condenser, the first valve having an open position and a closed position for selectively blocking flow through the tube;
   d. a second valve disposed along the tube at a location below the first valve having an open position and a closed position for selectively blocking flow through the tube, the first and second valves being spaced away from one another to define therebetween an aliquot collector of predetermined volume when the first and second valves are in their closed positions;
   e. a third valve disposed along the tube at a location below the second valve having an open position and a closed position for selectively blocking flow through the tube, the second and third valves being spaced away from one another to define therebetween a reaction chamber of predetermined volume when the second and third valves are in their closed positions;
   f. a catalyst for dissociating said peroxide in said aliquot, the catalyst being carried within the tube at a location disposed between the second and third valves;
   g. a pressure monitor operatively connected to the reaction chamber for detecting pressure changes resulting from said dissociation as a function of time, which pressure change is correlated to the concentration of peroxide in said sterilant, the pressure monitor including a timer and means for detecting a threshold pressure and an upper pressure, the pressure monitor being adapted to measure time change on the timer between detection of the threshold pressure and detection of the upper pressure; and
   h. a microprocessor operatively connected to the pressure monitor for calculating a peroxide concentration from said time change and a display for displaying the calculated peroxide concentration.

2. The apparatus of claim 1 wherein the first valve includes a level sensor for detecting when level of condensed sterilant in the tube is as high as or higher than the first valve.

3. The apparatus of claim 2 further comprising a valve controller adapted to close the first valve when the level sensor detects a level of condensed sterilant as high as or higher than the first valve.

4. The apparatus of claim 1 wherein the catalyst is retained in a porous enclosure, the porous enclosure being sized to prevent the enclosure from passing through the third valve when the third valve is in its open position.

5. The apparatus of claim 1 wherein the tube has a substantially constant inner diameter and the distance between the second and third valves is no less than the distance between the first and second valves.

6. The apparatus of claim 5 wherein the distance between the second and third valves is greater than the distance between the first and second valves.

7. An apparatus for measuring peroxide concentration in a gaseous sterilant, comprising:
   a. a condenser for condensing the gaseous sterilant into a liquid condensate;
   b. an aliquot collector of predetermined volume receiving condensate from the condenser;

c. a reaction chamber containing a catalyst for dissociating said peroxide in said aliquot; and d. a pressure monitor operatively connected to the reaction chamber for detecting pressure changes in the reaction chamber resulting from said dissociation as a function of time, which pressure change is correlated to the concentration of peroxide in said sterilant, the pressure monitor including a timer and means for detecting a threshold pressure and an upper pressure, the pressure monitor being adapted to measure time change on the timer between detection of the threshold pressure and detection of the upper pressure.

8. The apparatus of claim 7 further wherein the reaction chamber has a predetermined volume and receives the aliquot from the aliquot collector.

9. The apparatus of claim 8 wherein the pressure monitor is operatively connected to the reaction chamber for detecting said pressure changes.

10. The apparatus of claim 7 wherein the aliquot collector is disposed beneath the condenser.

11. The apparatus of claim 7 further comprising sampling means for conducting a sample of the gaseous sterilant from a sterilizing enclosure to the condenser.

12. The apparatus of claim 7 wherein the catalyst comprises a surface acting catalyst.

13. The apparatus of claim 12 wherein the catalyst comprises platinum.

* * * * *